(12) United States Patent
Nold et al.

(10) Patent No.: US 11,129,668 B2
(45) Date of Patent: Sep. 28, 2021

(54) COAGULATION AND DISSECTION INSTRUMENT WITH PIN ELECTRODES

(71) Applicant: Erbe Elektromedizin GmbH, Tuebingen (DE)

(72) Inventors: Bernhard Tobias Nold, Tuebingen (DE); Rolf Weiler, Tuebingen (DE); Peter Selig, Nehren (DE); Klaus Fischer, Nagold (DE); Lars Blobel, Ammerbuch (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 292 days.

(21) Appl. No.: 15/987,627

(22) Filed: May 23, 2018

(65) Prior Publication Data

US 2018/0338791 A1 Nov. 29, 2018

(30) Foreign Application Priority Data

May 24, 2017 (EP) ..................................... 17172876

(51) Int. Cl.
*A61B 18/00* (2006.01)
*A61B 18/14* (2006.01)

(52) U.S. Cl.
CPC ...... *A61B 18/1442* (2013.01); *A61B 18/1477* (2013.01); *A61B 2018/0063* (2013.01);
(Continued)

(58) Field of Classification Search
CPC ............ A61B 18/1442; A61B 18/1477; A61B 2018/00404; A61B 2018/00589;
(Continued)

(56) References Cited

U.S. PATENT DOCUMENTS 5,269,780 A * 12/1993 Roos .................. A61B 18/1442
606/42
5,944,718 A * 8/1999 Austin ............... A61B 18/1445
606/48
(Continued)

FOREIGN PATENT DOCUMENTS

CN 104042330 A 9/2014
CN 105395248 A 3/2016
(Continued)

OTHER PUBLICATIONS

European Search Report for corresponding European Application No. 17172876.9, dated Nov. 24, 2017, 9 pages.
(Continued)

*Primary Examiner* — Linda C Dvorak
*Assistant Examiner* — Nils A Potter
(74) *Attorney, Agent, or Firm* — Fitch, Even, Tabin & Flannery LLP

(57) ABSTRACT

The instrument comprises a jaw arrangement with two jaws that have, on their side facing the counter-electrode arrangement, rounded or flat electrode surfaces. The counter-electrode arrangement comprises at least one counter-electrode surface that may be rounded or flat. One of the electrode surfaces has a band edge preferably bordered by an insulator on one side, said band edge being adjacent to the adjacent electrode surface of the jaw arrangement. The counter-electrode surface has a band edge adjacent to the insulator facing the band edge of the one electrode surface. The band edges of the electrode surfaces acting as the coagulation surfaces are close enough such that they form cutting edges that develop a cutting effect with low voltages that are otherwise suitable only for coagulation. Accordingly, it is possible to provide fusion instruments that are extremely
(Continued)

delicate, display lower thermal inertia and an excellent fusion and cutting effect.

14 Claims, 6 Drawing Sheets

(52) U.S. Cl.
CPC ............. *A61B 2018/00404* (2013.01); *A61B 2018/00589* (2013.01); *A61B 2018/00601* (2013.01); *A61B 2018/00607* (2013.01); *A61B 2018/1407* (2013.01); *A61B 2018/1467* (2013.01)

(58) Field of Classification Search
CPC .. A61B 2018/00601; A61B 2018/0063; A61B 2018/1407; A61B 2018/1467; A61B 2018/00607; A61B 17/29; A61B 18/12; A61B 18/14
USPC ........................................................ 606/51
See application file for complete search history.

(56) References Cited

U.S. PATENT DOCUMENTS

| | | | | |
|---|---|---|---|---|
| 6,059,782 A * | 5/2000 | Novak | ............... | A61B 18/1442 606/48 |
| 6,113,598 A * | 9/2000 | Baker | ............... | A61B 18/1445 606/38 |
| 6,152,923 A * | 11/2000 | Ryan | ................. | A61B 18/1445 606/51 |
| 6,478,794 B1 | 11/2002 | Trapp | | |
| 7,070,596 B1 * | 7/2006 | Woloszko | .......... | A61B 18/1482 606/41 |
| 9,717,548 B2 | 8/2017 | Couture | | |
| 10,617,464 B2 | 4/2020 | Düppuis | | |
| 2011/0130757 A1 * | 6/2011 | Horlle | ................ | A61B 18/1445 606/48 |
| 2016/0066980 A1 * | 3/2016 | Schall | ................ | A61B 18/1445 606/45 |
| 2017/0202609 A1 * | 7/2017 | Shelton, IV | ....... | A61B 18/1445 |

FOREIGN PATENT DOCUMENTS

| | | |
|---|---|---|
| CN | 105578980 A | 5/2016 |
| DE | 102008030285 A1 | 12/2009 |
| EP | 1051120 B1 | 5/2004 |
| EP | 1089664 B1 | 9/2005 |
| RU | 2080094 C1 | 5/1997 |
| WO | 9940861 A1 | 8/1999 |
| WO | 2016088017 A1 | 6/2016 |

OTHER PUBLICATIONS

Chinese Office Action and Search Report dated Jul. 28, 2020, in corresponding Chinese Application No. 201810500301.9, with English translation (15 pages).

Russian Office Action dated May 31, 2021, in corresponding Russian Application No. 2018118344/14(028624), with machine English translation (17 pages).

* cited by examiner

COAGULATION AND DISSECTION INSTRUMENT WITH PIN ELECTRODES

CROSS-REFERENCE TO RELATED APPLICATION(S)

This application claims the benefit of European Patent Application No. 17172876.9 filed May 24, 2017, the contents of which are incorporated herein by reference as if fully rewritten herein.

TECHNICAL FIELD

The invention relates to an electrosurgical instrument, in particular for vessel fusion.

BACKGROUND

In practice, electrosurgical instruments are used for severing biological tissue and for the haemostatic treatment of cut edges. In particular, it is possible to use electrosurgical instruments for the closure of vessels, for example blood vessels or other hollow organs. The closure of vessels is typically done in that the vessel to be fused is clamped between the jaws of a forceps-like instrument and energized, so that a coagulation effect will occur. Furthermore, the closed vessel can be severed at the closure site, e.g., by a mechanical or electric knife.

From document U.S. Pat. No. 5,944,718 a fusion instrument has been known, said instrument comprising two pin-like electrodes that have a circular cross-section and are held parallel to each other in a fixed spatial relationship. Both electrodes are associated with a counter-electrode that bridges the distance between the two pin-like electrodes and has two convexly rounded counter-electrode sections for the fusion of vessels, whereby a flatter electrode section is arranged between said sections. In this configuration, this instrument can be used for the fusion of vessels.

The counter-electrode of this instrument is rotatably attached to a holder in such a manner that the convexly rounded electrode surfaces of the counter-electrode can be rotated away from the electrodes. Instead, then a narrow edge is active that can immerse between the round rod electrodes. Concave flank regions adjoin the narrow edge.

Furthermore, an instrument for fusing and severing vessels has been known from publication EP 1 089 664 B1, said instrument having branches on of U-shaped, bent round wires or toothed wires. In doing so, the electrode and the counter-electrode are arranged so as to be in alignment with each other in such a manner that a vessel grasped and coagulated between the electrode and the counter-electrode can be slit open by an axially advanceable flat cutting electrode.

Furthermore, publication EP 1 051 120 B1 discloses a fusion instrument comprising a bracket-shaped wire electrode and an also bracket-shaped counter-electrode that is in alignment with the latter. Between the two jaws of the bracket shaped electrode and counter-electrode there is a wide free space. A wire cutting electrode may immerse through this free space and effect a cut through a fused vessel.

From publication U.S. Pat. No. 5,269,780 an instrument is known that is used for cutting or coagulating biological tissue. This instrument comprises two electrodes having a round cross-section, said electrodes being held parallel at a distance from each other. The counter-electrode that is provided is a cutting electrode having a round cross-section, however with a smaller diameter than the two electrodes. The cutting electrode may immerse between the two electrodes, which is why this instrument is suitable for the severing of tissue however not for the fusion of vessels.

Publication WO 2016/088017 A1 describes a coagulation instrument having branches that are in alignment with each other and have a round cross-section. The electrodes are provided with insulator inlays that are arranged asymmetrically relative to each other. This is to generate local current concentrations to produce a cutting effect.

Furthermore, publication U.S. Pat. No. 6,152,923 discloses a fusion instrument with six flat electrodes arranged in aligned pairs. While the middle electrode pair is used for severing vessels, the electrode pairs arranged on both sides are fusion electrodes that are used for closing the separated ends of the cut vessel.

In the course of the development of vessel fusion instruments it is of importance to achieve the fastest possible and secure seal of vessels. At the same time, there is a trend toward miniaturization including the laparoscopic use of fusion instruments or even the use in a trocar or catheter. However, it has been found that the dimensions of the known fusion instruments cannot simply be reduced on the same scale because even instruments that are reduced in size must be capable of treating the same size of vessels as before. In doing so, particular attention is paid to the secure vessel closure. If an electric cut is to be performed, it is possible for insulation problems to occur with miniaturized instruments due to the height of the usually required cutting voltage. Furthermore, the miniaturization can lead to considerable flexibility, i.e., mechanical resilience of the branches. However, due to the aim for miniaturization and the concomitant increased precision requirements, this is problematic.

SUMMARY

Considering this, it is the object of the invention to provide a concept for a fusion instrument with which particularly small designs and, optionally, also additional advantages can be implemented.

This object may be achieved with the instruments described and claimed herein.

The instrument according to one form of the invention is a coagulation and dissection instrument with pin electrodes, the jaws of said instrument being formed by a jaw arrangement and a counter-jaw arrangement. The jaw arrangement comprises a first jaw with a first electrode surface and a second jaw with a second electrode surface, these being held in a fixed spatial relationship relative to each other. The counter-jaw arrangement comprises at least one counter-jaw. At least one, i.e., the first jaw, the second jaw and the counter-jaw, has an electrode surface that is arranged off-center relative to the center line E that is defined by the direction of movement R of the jaw or counter-jaw and its cross-sectional center. As a result of this, the counter-jaw be assigned a double function: With the first jaw, it forms a fusion gap and with the second jaw, it forms a cutting gap. Because, however, the at least one, preferably pin-shaped, counter-jaw is opposed by at least two also preferably pin-shaped jaws, the jaws and count-jaws can align relative to each other, in which case the counter-jaw centers itself between the jaws. Consequently, even with a certain springy resilience of the jaws and the at least one counter-jaw, it is possible to achieve precise work results because the jaws and counter-jaws support each other.

The jaw arrangement and the counter-jaw arrangement are configured and positioned and moved relative to each other in such a manner that they can grasp and compress between them biological tissue and compress said tissue in particular in such a manner that the lumen in the vessel is closed completely. Preferably, the jaw arrangement and the counter-jaw arrangement are configured and held in such a manner that they, when the branches are closed, i.e., when they are moved toward each other, meet each other in an offset manner. To accomplish this, the counter-jaw arrangement preferably comprises at least one jaw that is configured so as to be wider than the distance between the first and the second jaws, so that the counter-jaw does not fit through the gap formed by the jaws. If several counter-jaws are provided, the distance between the counter-jaws is preferably smaller than the width of one jaw. The widths of the above-mentioned distances are measured in a direction transverse with respect to the direction of movement of the jaws while the instrument is being opened and closed.

Preferably, the second jaw of the jaw arrangement comprises an electrically conductive electrode section and an insulated section that is arranged on the side of the second jaw facing the first jaw. Furthermore, the counter-jaw preferably has an electrically conductive counter-electrode section and an electrically insulated counter-section which is arranged on the side facing away from the jaw. The electrically conductive electrode section of the second jaw of the jaw arrangement may have an edge in the vicinity of the insulated section. As a result of this, a current concentration can be produced on the edges of the electrodes, said current concentration being disposed for initiating a tissue cut.

Referring to the instrument according to the invention, the counter-jaw has a circular cross-section, for example, in which case the distance between the first jaw and the second jaw is smaller than the diameter of the counter-jaw. In this manner, it can be ensured that the two jaws and the associate counter-jaw have the same stiffness or resilience. In doing so, the cross-sectional surface of the counter-jaw is preferably at most as large as the sum of the two cross-sectional surfaces of the two jaws. In doing so, it is of advantage if the cross-sectional surface of the counter-electrode is at most as large as the sum of the two cross-sectional surfaces of the two electrodes. In particular, this avoids a one-sided cooling of the vessel that is to be fused. The coagulation acts particularly uniformly. In doing so it is advantageous if the two jaws and counter-jaws display the same thermal behavior, i.e., heat up and cool down at the same heating and cooling rate when used. In doing so, it is advantageous if the jaws and the counter-jaws display comparable heat capacity.

The circular cross-section represents only one possible embodiment. The jaws and counter-jaws may have cross-sections deviating from the circular form, in which case, preferably in the region of contact of the jaws, convex surfaces are provided. On the rear side, i.e., on the side away from the working gap, the jaws may be connected by one or several strips. For example, the jaw arrangement may be a flat, continuous part, for example made of plastic material, that has two strip-shaped, preferably rounded, elevations at a distance from each other.

The center of the counter-jaw is preferably located on a center line on which also the jaws of the jaw arrangement are located on different sides at equal distances. In doing so, the jaws may be arranged on the same level—i.e., reflected on the center line—or on different levels.

In a preferred instrument, the first electrode surface and the second electrode surface may be electrically connected to each other. This is true in particular if the cutting voltage corresponds to the coagulation voltage. The physiological effect (cutting/coagulating) is determined by the electrode form. The concept according to the invention allows the use of low cutting voltages, for example, of below 300 $V_p$, preferably below 250 $V_p$. This minimizes the otherwise common insulation problems that could occur, in particular, in the event of the miniaturization of the instruments. The instrument according to the invention can be set up for laparoscopic surgery, where only little design space, e.g., a diameter of only 5 mm, is available for the instrument.

In a preferred embodiment, the counter-jaw arrangement comprises two counter-jaws, wherein only one is disposed for coagulation, while the other performs an additional cutting function. The counter-jaw performs a cutting and coagulating function.

Preferably, the instrument has two jaws and two counter-jaws, in which case the jaws of the jaw arrangement and the counter-jaws of the counter-jaw arrangement are arranged so as to be laterally offset with respect to each other. Consequently, the jaws and counter-jaws are self-centering. Then, the counter-electrodes, together with the electrodes, fix two coagulation gaps and one cutting gap, so that coagulation and cutting occur in different positions.

Due to the mentioned measure, the electrodes and the counter-electrode(s) can be configured in an extremely slim manner and be surprisingly efficient in view of their fusion effect. Preferably, there is no planar surface coming into contact with the tissue at the working gap. In particular, no pairing of planar surfaces is provided, i.e., the coagulation gap displays a non-constant gap-size transversely with respect to the jaws. Thus, a miniaturization is largely possible, in which case such miniaturized fusion instruments can be used for sealing vessels having the size that required larger instruments in the past.

The inventive embodiment of the jaw arrangement and the counter-jaw arrangement represents a concept that is not sensitive to manufacturing tolerances. The electrodes and counter-electrodes are configured so as to be mutually centering when being closed. Furthermore, the vessels are grasped very firmly by the electrodes and the at least one counter-electrode, so that the risk of slipping is minimized or eliminated.

Furthermore, the concept according to the invention results in a particularly narrow design that allows the user a good view onto the coagulation instrument and the vessel to be treated, in particular during laparoscopic or endoscopic procedures.

In a preferred embodiment the counter-electrode has a circular cross-section, wherein the distance between the first electrode and the second electrode from each other is smaller than the diameter of the counter-electrode. In doing so, a secure seal on the vessel is achieved.

Alternatively, the counter-electrode may have a cross-section with one or more corners, wherein the center distance $A_m$ of the two non-concave, preferably flat, sections of the counter-electrode are preferably larger than the distance of the two electrodes from each other. With this, it is also possible to attain a slim, highly effective fusion instrument.

Referring to the instrument according to the invention, the jaws of the jaw arrangement and the counter-jaws of the counter-jaw arrangement may be arranged so as to be laterally offset relative to each other. In doing so, respectively one jaw of a jaw pair may be centrally located on a line between the jaws of the other jaw pair. When the instrument is being closed, the jaws are automatically centered relative to each other. Thus, safe work is possible, even with instruments that have very small dimensions and are delicate and/or slightly flexible.

BRIEF DESCRIPTION OF THE DRAWINGS

Additional details of advantageous embodiments of the invention can be inferred from the description or claims and the drawings. They show in:

DETAILED DESCRIPTION

Figure 1:
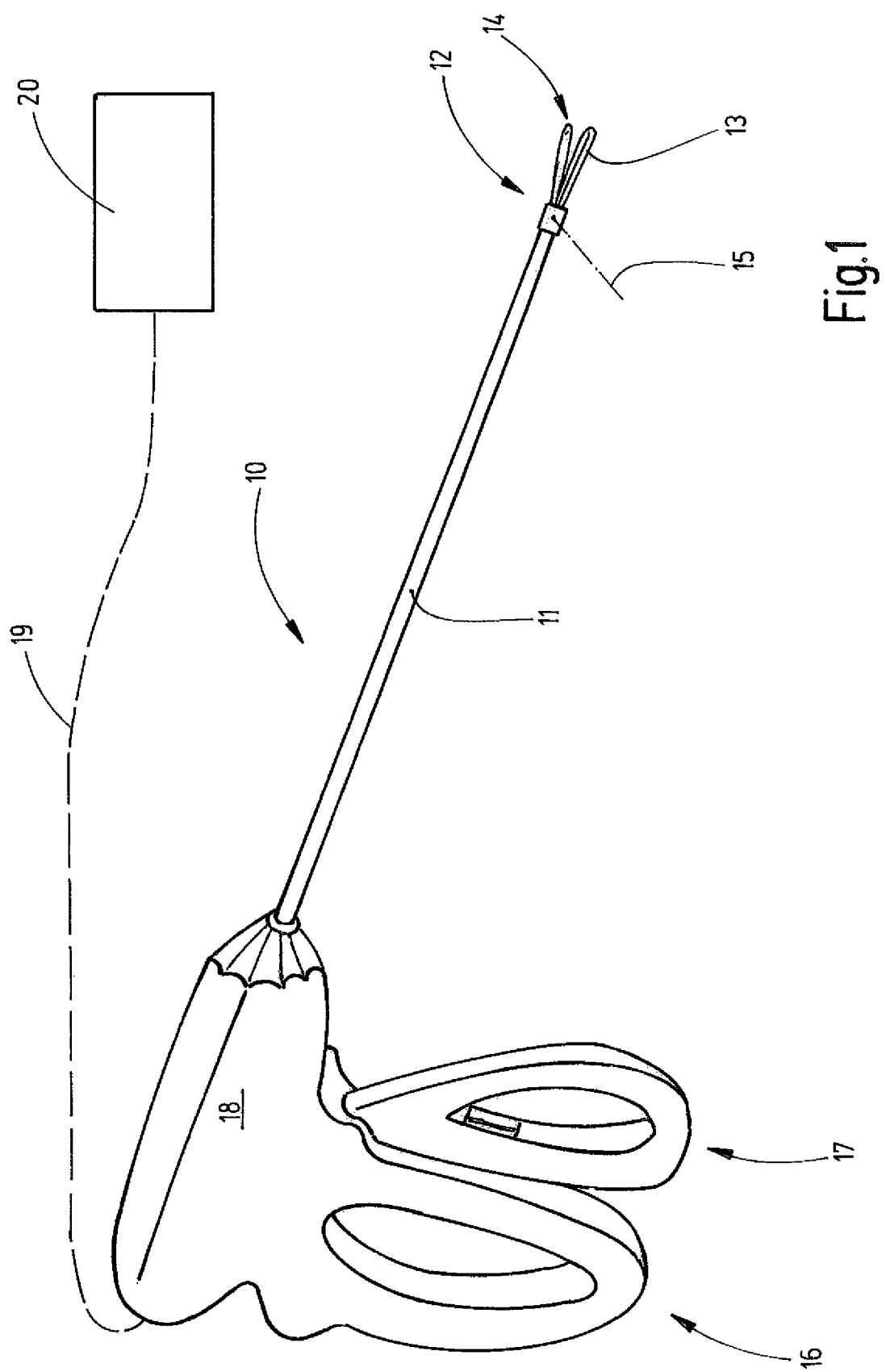
FIG. 1 a schematized representation, partially in perspective, of the fusion instrument according to the invention and its supply apparatus.

FIG. 1 shows an instrument 10 that can be used for closing and sealing vessels of human or animal patients or also for severing and/or coagulating tissue. The instrument can be configured for the open surgical use, as laparoscopic instrument or as endoscopic instrument. FIG. 1 shows the instrument 10 as an example for the laparoscopic use. For this, it comprises a tool 12 held on the distal end of a shaft 11, said tool comprising a jaw arrangement 13 and a counter-jaw arrangement 14. The jaw arrangement 13 and/or the counter-jaw arrangement 14 are held so as to pivotable about an axis 15 oriented transversely with respect to the shaft 11, so that the jaw arrangement 13 and the counter-jaw arrangement 14 can be moved toward each other and away from each other. For the targeted movement of said arrangements, there is provided a handle 16 that is associated with an actuating lever 17. Due to the targeted movement of the actuating lever 17, the tool 12 closes and tissue, e.g., a vessel, can be held and clamped between the jaw arrangement 13 and the counter-jaw arrangement 14.

While the handle 16 is or may be part of a housing 18 that accommodates the proximal end of the shaft 11, the actuating lever 17 is pivotally or otherwise movably held on this housing 18. At least one actuating element extends through the shaft 11 for moving the jaw arrangement 13 and/or the counter-jaw arrangement 14. Furthermore, electrical lines extend through the shaft 11, the housing 18, as well as through a cable 19, in order to connect the tool 12 to an apparatus 20 for operating the instrument 10.

Figure 2:
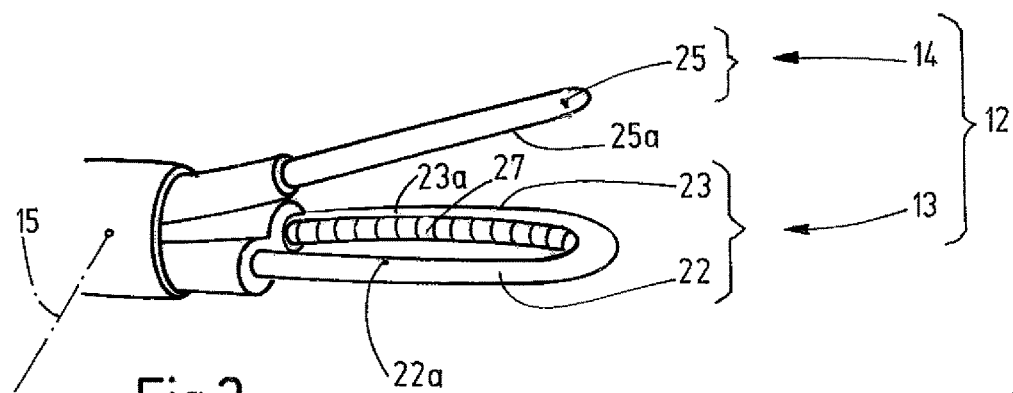
FIG. 2 a schematic representation of the electrodes and the counter-electrode of the fusion instrument according to FIG. 1.

The tool 12 is further illustrated in FIG. 2. The lower jaw arrangement 13 comprises two jaws 22, 23 that are straight or slightly curved in longitudinal direction and that are, e.g., wires or rods. Preferably, the jaws 22, 23 extend parallel to each other at a fixed distance. They may have a constant, matching cross-section and be mechanically and electrically connected on their distal end to each other by, e.g., a u-shaped bent section, or be only mechanically connected by an electrical insulator. Referring to the present exemplary embodiment, the jaw arrangement 13 is a wire bracket. However, the jaws 22, 23 may also taper in distal direction, be arranged at an acute angle with respect to each other, and/or be separated from each other on their distal end. Independently thereof, it is also possible to alternatively not connect the two jaws 22, 23 on their distal end. However, they are held in a fixed spatial relationship, preferably parallel to each other.

Figure 3:
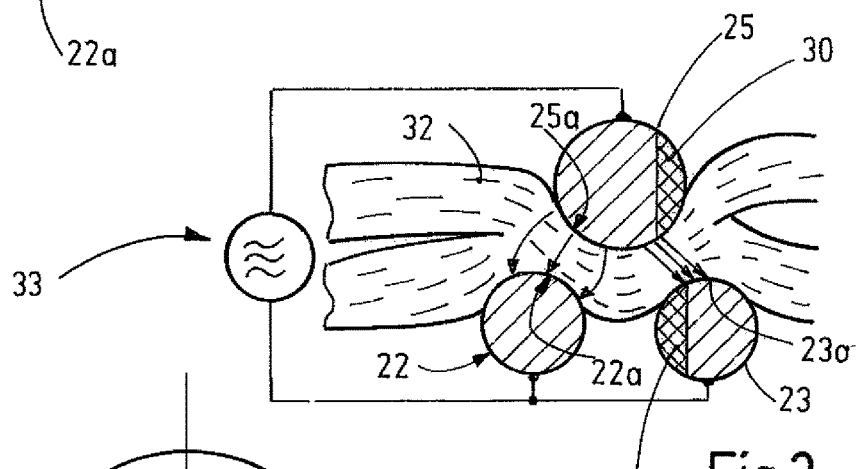
FIG. 3 a schematized cross-sectional representation of the electrodes and the counter-electrode of the fusion instrument according to FIGS. 1 and 2, during the fusion of a vessel.

The jaws 22, 23 comprise electrically conductive electrode surfaces 22a, 23a that are connected or can be connected to one terminal of an electrical source of the apparatus 20, as illustrated in FIG. 3. In this exemplary embodiment, the electrode surfaces 22a, 23a are represented by the not insulated, exposed surface of the jaws 22, 23. Only one of the jaws 22, 23—in this case jaw 23—is provided, on its side facing the other jaw, with an insulator 27 that engages in the contour of the jaw 23. The insulator 27 directly adjoins a band edge 28 of the electrode surface 23a (FIG. 4).

Figure 7:
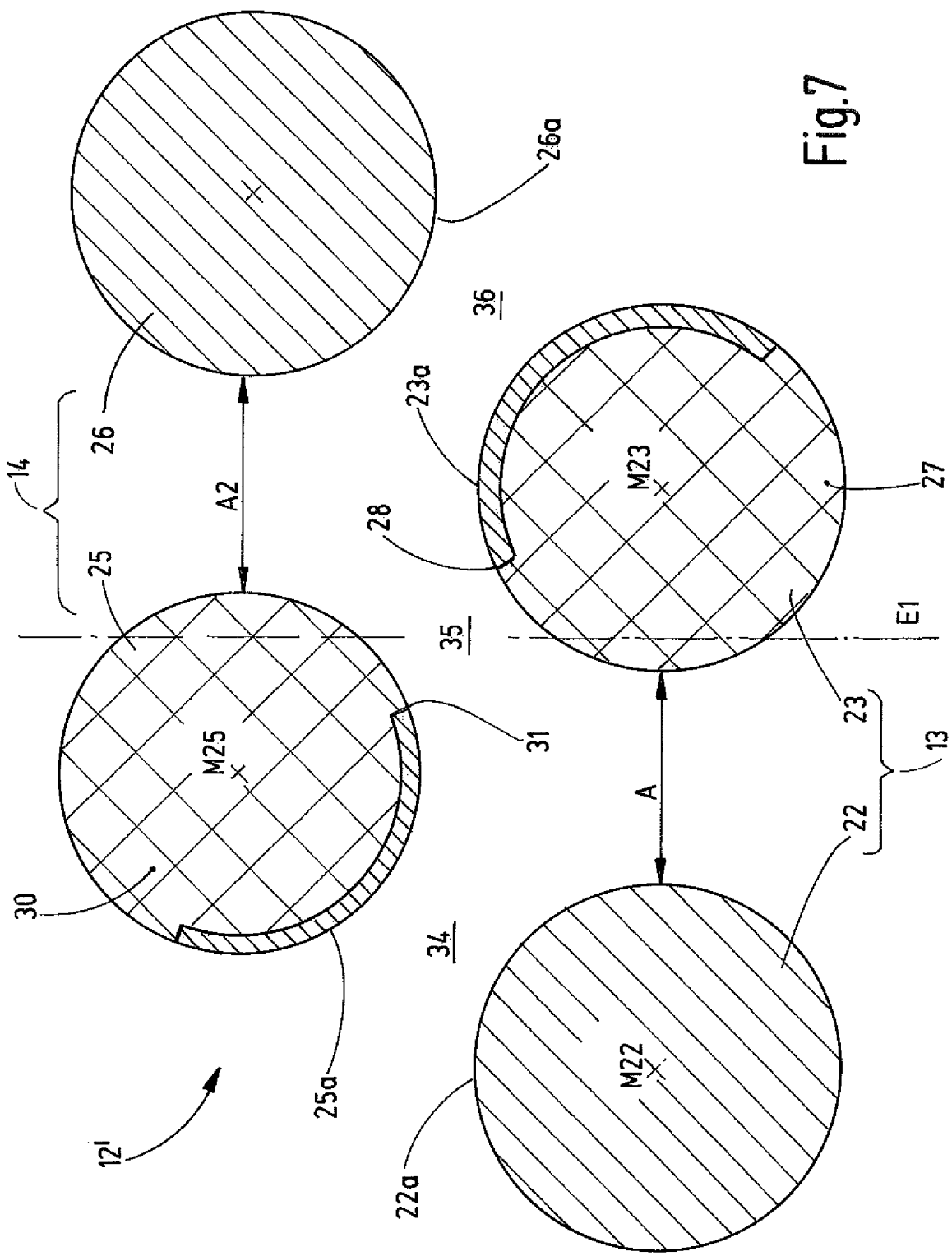
Figure 10:
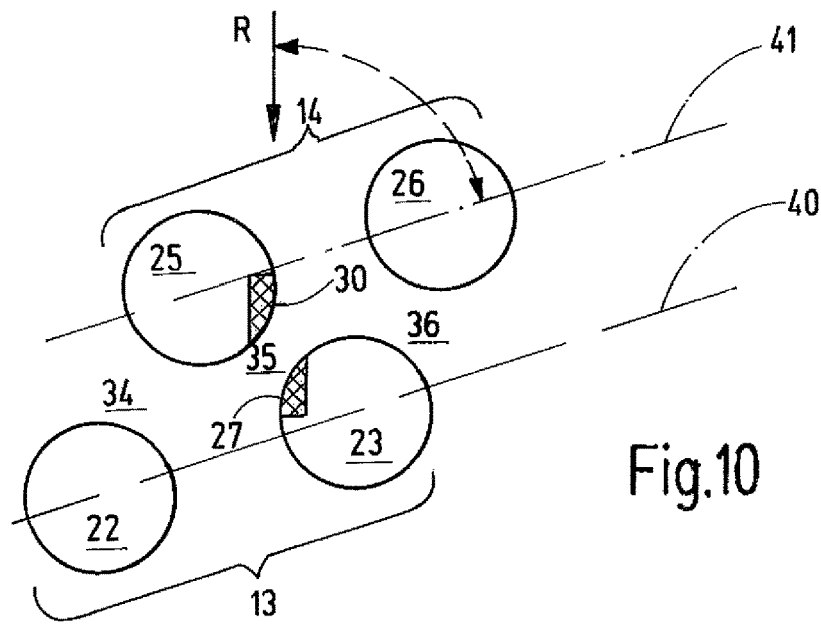
FIG. 10 schematized cross-sectional representations of a further modified jaw and counter-jaw arrangement.

The counter-jaw arrangement 14 associated with the jaw arrangement 13 comprises at least one counter-jaw 25 that is straight or slightly curved in longitudinal direction and, in modified embodiments, comprises several counter-jaws 25, 26 as can be inferred from FIG. 7 or 10. The counter-jaw 25 has an electrically conductive counter-electrode surface 25a the surface of which is arcuate in cross-section. The cross-section of the counter-jaw 25 may be unchangeable in longitudinal direction; alternatively, the counter-jaw 25 may also taper slightly in longitudinal direction.

On its side adjacent to the jaw 23 and remote from the jaw 22, the counter-jaw 25 is provided with an insulator 30 that adjoins a band edge 31 of the counter-electrode surface 25a and engages in the contour of the counter-jaw 25. The insulator 30 overlaps the insulator 27—relative to the direction of movement R. In contrast, the electrode formed by the electrode surface 23a and the electrically conductive part of the jaw 23 does not overlap with the electrode that is formed by the counter-electrode surface 25a and the electrically conductive part of the counter-jaw 25.

Figure 4:
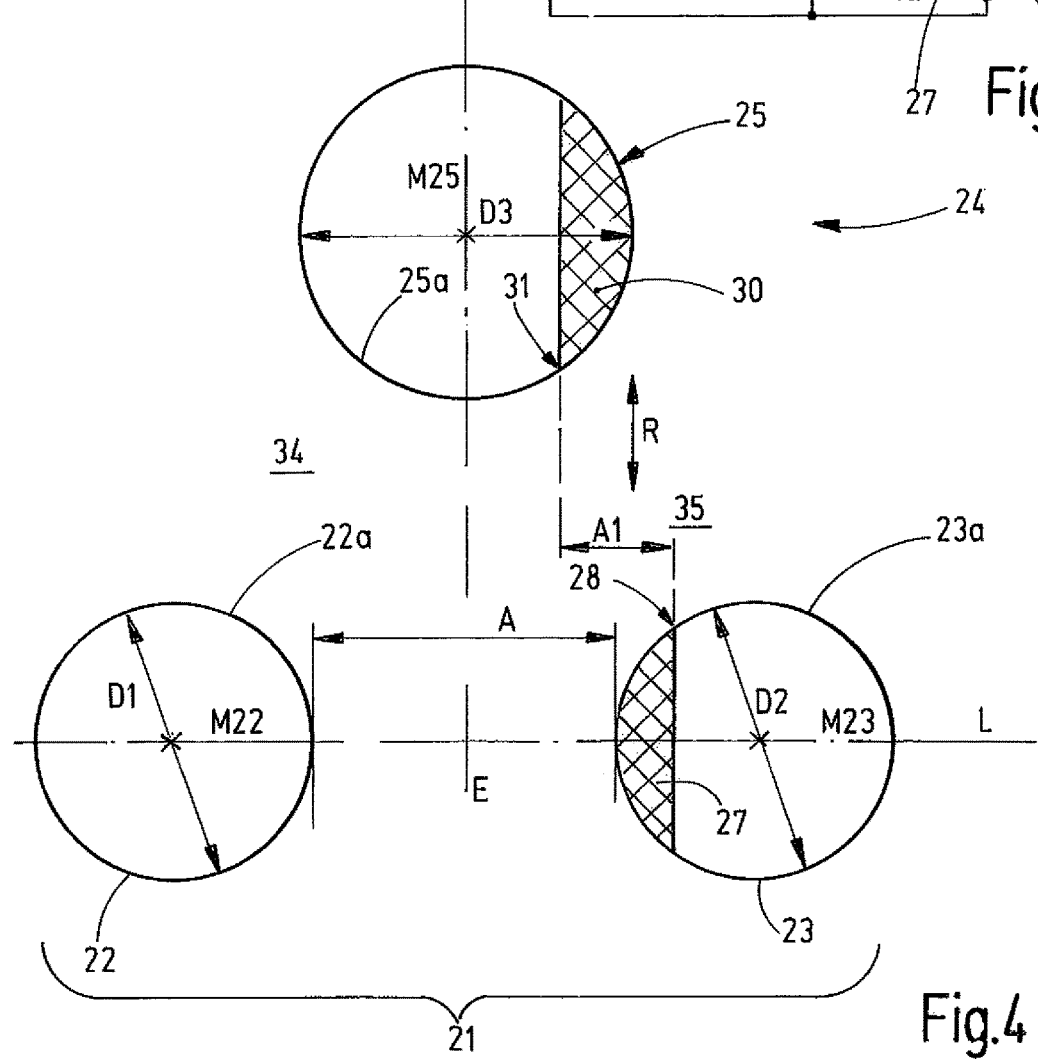
FIG. 4 electrodes and counter-electrodes in an enlarged cross-section to illustrate dimensional relationships.

The enlarged representation of the cross-sections of the jaws 22, 23 and the counter-jaw 25 shown in FIG. 4 shows a few dimensional relationships thereof with reference to the example of circular cross-sections. The jaws 22 and 23 preferably have the same or also slightly different diameters D1 and D2 and are arranged at a distance A from each other. The distance A defines the clearance between the electrodes 22, 23 and is measured transversely with respect to a direction of movement R, in which the counter-jaw 25 can be moved relative to the jaws 22, 23 and/or the jaws 22, 23 can be moved relative to the counter-jaw 25.

The jaws 22, 23 are arranged symmetrically with respect to a center line E. The center line E is oriented parallel to the direction of movement R and extends through the center M25 of the cross-section of the counter-jaw 25. In non-circular cross-sections, the center M25 is represented by the center of area of the cross-sectional surface. The same applies to the centers M22 and M23 of the cross-sectional surfaces of the jaws 22, 23. The centers M22, M23 are located on a line L that intersects the center line preferably at a right angle. However, the line L may also be fixed at an acute angle with respect to the center line, so that the distance of the jaw 23 from the counter-jaw 25 is smaller than the distance of the jaw 22 from the counter-jaw 25. These relationships represent the geometric ideal case.

Deviations may occur due to production tolerances, elasticities of the elements and because of deformations caused by use.

The counter-jaw 25 has a diameter D3 that is preferably greater than the distance A and is located centrally symmetrically on the center plane or the center line E. Consequently, the counter-electrode 25 is in contact with at least one of the electrodes 22, 23, preferably both, if it is moved as closely as possible toward them. Consequently, the jaw arrangement 13 and the counter-jaw arrangement 14 can grasp between them large, voluminous as well as highly delicate fine vessels 32, in which case the relationships according to FIG. 3 will occur. This is true, in particular, when the jaws 22, 23 and/or the counter-jaws 25 are configured so as to be somewhat elastically yielding. The jaws 22, 23 and the counter-jaw 25 are able to coagulate even extremely small vessels due to their resilient adaptation.

The electrode surface 22a of the jaw 22 is a coagulation surface curved at a radius of D1 and a radius of D2 that faces the counter-electrode 25. The counter-electrode surface 25a of the counter-electrode 25 is curved at a radius of D3 and faces the electrode surface 22a. The vessel 32 is grasped between the electrode surface 22a and the counter-electrode surface 25a and energized. As a result of the only gentle curvature of the electrode-surfaces 22a, 25a and the relatively large-area contact between the electrode surfaces 22a, 25a and the vessel 32, the vessel between the electrode surfaces 22a, 25a is compressed and coagulated between the closed branches, as is illustrated in FIG. 3.

In contrast, the vessel 32 between the jaw 23 and the counter-jaw 25 is at least partially grasped and compressed between the insulators 27, 30. The band edges 28, 31 have a very small radius of curvature that is clearly smaller than the radii of curvature of the electrode surfaces 22a, 23a, 25a. The distance A1 measured between the band edges 28, 31 in the direction of line L is preferably 0.1 mm to 0.75 mm. Thus, an electrical short circuit between the electrode surfaces 23a, 25a is precluded, on the one hand, and a high current density in the tissue can be achieved, on the other hand.

Figure 8:
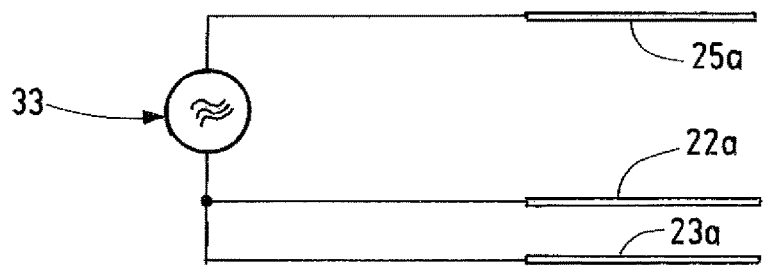
FIGS. 8 and 9 simplified diagrams to illustrate the voltage or current application to the fusion instrument.

The instrument 10 described so far can be used for the preparation of organs, tumors, for cutting tissue or also for (one-sided) closing and severing vessels as follows:

As shown in FIGS. 3 and 8, the instrument 10 is connected to an electrical source 33. The electrode surfaces 22a, 23a are connected to a terminal of the source 33, and the counter-electrode surface 25a is connected to another terminal of said source. The electrical source 33 is preferably an RF generator that outputs a voltage having a frequency of several 100 kHz and a voltage between 80 $V_p$ and 500 $V_p$ (preferably between 200 $V_p$ and 250 $V_p$). During use, the tissue 32 is grasped between the counter-electrode surface 25a and the electrode surfaces 22a, 23a, whereupon the counter-jaw arrangement 14 and the jaw arrangement 13 are moved toward each other when the tool 12 is being closed such that all lumens of the tissue 32 are closed. At the latest at this time or shortly thereafter, the generator 33 is activated, so that the two current paths starting at the counter-electrode surface 25a and the band edge 37 extending through the tissue 32 to the electrode surfaces 22a, 23a are energized, and the tissue compressed there is heated by the action of the current, coagulated and cut. The electrode surface 22a and the counter-electrode surface 25a thus delimit a coagulation gap 34.

In conjunction with this it has been found that, with the use of the electrode surface 22a and the counter-electrode surface 25a, and diameters D1, D3 of 0.3 mm to 1.5 mm, preferably 0.4 mm to 1.0 mm, it is possible to achieve a vessel seal displaying high bursting strength (e.g., over 120 mmHg) within a short time (e.g., less than 4 seconds).

Each of the electrode surfaces 23a, 25a has a band edge 28 or 31 only on one side, this resulting in a current concentration and thus the formation of a cutting gap 35 between the insulators 27, 30. Using the same treatment time and the same activation, the same voltage results in the coagulation gap for tissue fusion and in the cutting gap 35 for tissue dissection. Alternatively, it is also possible to essentially coagulate only during a first phase and to essentially cut only during a second phase.

Figure 5:
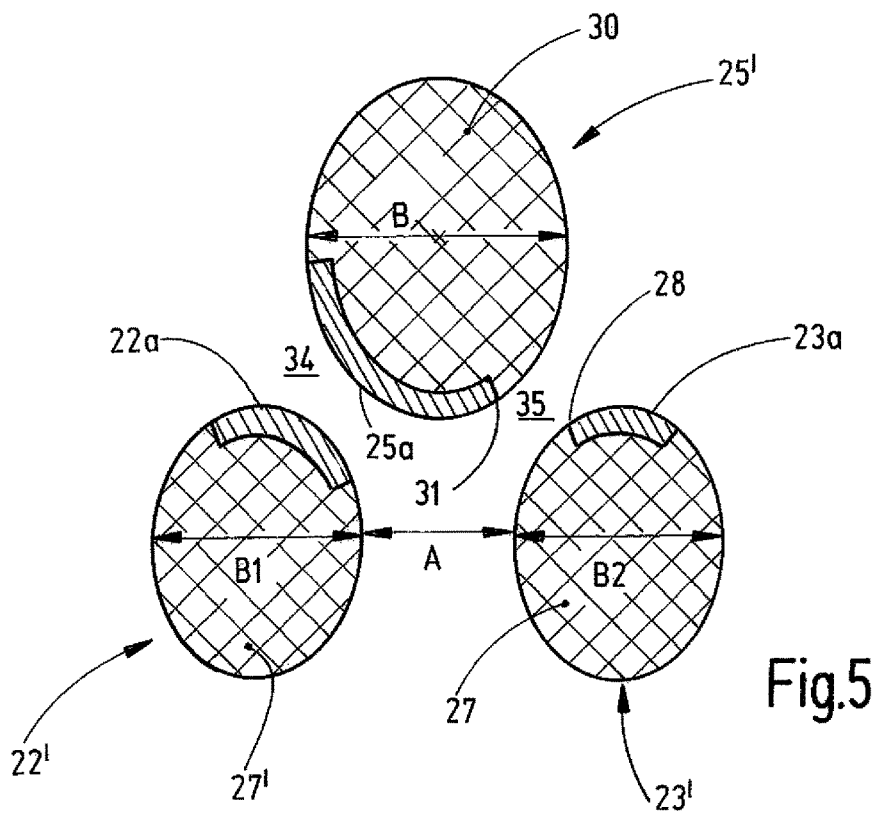
FIGS. 5 to 7 schematized cross-sectional representations of modified jaw and counter-jaw arrangements.

The respective cross-sections of the jaws 22, 23 and/or the counter-jaws 25 may deviate from their circular form, as can be inferred, for example, from FIG. 5. Furthermore, it is possible to configure each of the jaws 22 and 23' and/or counter-jaws 25' as insulators 27, 27', 30 and to provide the electrode surfaces 22, 23a and/or the counter-electrode surface 25a on the electrically conductive coatings or metal inlays that are applied to the jaws 22', 23' and/or the counter-jaws 25' made of the insulating material. In the modified instrument 10 according to FIG. 5, the distance A is again smaller than the width B of the counter-electrode 25', measured in the same direction. Preferably, also the widths B1, B2 of the jaws 22', 23' that are to be measured in the same direction as the distance A1 and the width B, are greater than the distance A. Other than that, the descriptions given hereinabove regarding FIGS. 1 to 4 and 8 apply analogously.

Figure 6:
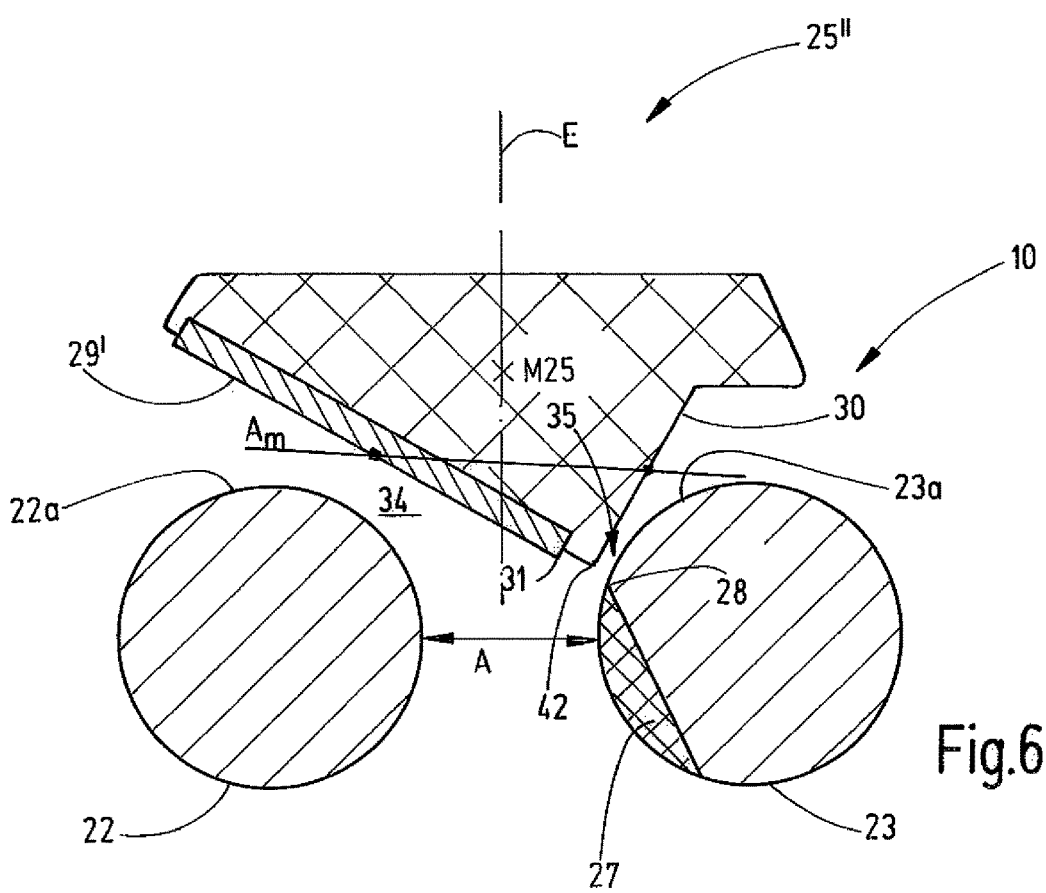

FIG. 6 shows a further modified exemplary embodiment. In this case, the jaws 22, 23 may have any of the aforementioned forms, for example according to FIG. 4 or according to FIG. 5. In this case, the counter-electrode 25" has two non-concave sections—i.e., flat sections 25a, 30' in the example—wherein the connection 42 between them may be represented by a corner or edge having a small radius of curvature. The sections 25a', 30' display a center distance $A_m$ that, in turn, is greater than the distance A between the jaws 22, 23. With this configuration it is also possible to attain the advantageous effects of the concept according to the invention outlined hereinabove.

All embodiments of the instrument 10 have in common that the counter-electrode surface 25a is arranged off-center relative to the center line E. FIG. 6 illustrates this on an instrument 10 having a flat counter-electrode surface 25a. As depicted, the insulator 27 may be provided or, alternatively, also be omitted. However, it promotes the cutting effect.

FIG. 7 shows another, further developed, embodiment. To the extent that it corresponds to the embodiment according to FIGS. 2 to 5, reference is made to the relevant parts of the description with reference to the same reference signs. Additionally, the following applies:

Whereas the jaws 22, 23 in FIG. 4 are arranged symmetrically with respect to the center plane E or the center line E, the center plane or center line E1 in the embodiment according to FIG. 7 extends preferably off-center through the counter-jaw 25 and the jaw 23. The jaw arrangement 13 and the counter-jaw arrangement 14 according to FIG. 7 represent an asymmetrical arrangement. The counter-jaw arrangement 14 comprises one pair of counter-jaws 25, 26 that is laterally offset relative to the pair of jaws 22, 23, in which case, during closing, the counter-jaw 25 centers itself between the jaws 22, 23 and the jaws 23 between the counter-jaws 25, 26. The distance A2 between the counter-jaws 25, 26 may be the same as the distance A between the jaws 22, 23 or also deviate therefrom; in particular, it may be selected to be somewhat greater. All embodiments and options described hereinabove apply accordingly in view of the form and arrangement of the jaws 22, 23, as well as the form and arrangement of the counter-jaws 25, 26.

Referring to the configuration according to FIG. 7, a total of two coagulation zones 34, 36 and an interposed cutting gap are defined, namely, respectively in pairs between the jaw 22 and the counter-jaw 25 (coagulation region 34); between the counter-jaw 25 and the jaw 23 (cutting region 35); between the jaw 23 and the counter-jaw 26 (coagulation region 36). With the use of such an electrode configuration, it is possible to fuse vessels and coagulate tissue. In doing so, the electrode surfaces 22a, 23a can be connected to one terminal and the counter-electrode surfaces 25a, 26a to another terminal of the source 33.

Figure 9:
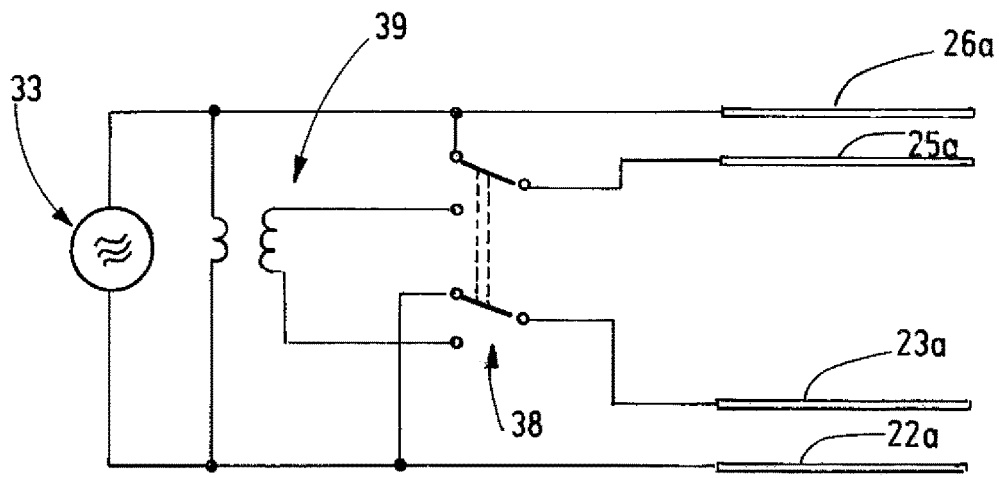

However, in a further modified embodiment, it is possible to apply different currents to the coagulation regions 34, 36 and the cutting region 35. To do so, for example, a supply circuit according to FIG. 9 may be used. It comprises a switch device 38 with the use of which the electrode surface 23a and the counter-electrode surface 25a can be connected, as needed, either to the same supply voltage as the electrode surfaces 22a and the counter-electrode surface 26a, or to a higher supply voltage. Said voltage may be provided by a source 39 that is a transformer, for example. Said transformer may be arranged in the housing 18 or also in the apparatus 20.

For example, the tool 12' according to FIG. 7 is operated as follows:

First, a biological tissue, e.g. a vessel between the jaw arrangement 13 and the counter-jaw arrangement 14 is grasped and compressed. Once this is done, the electrode surfaces 22a, 23a are connected to a terminal of the source 33, and the counter-electrode surfaces 25a, 26a are connected to another terminal of the source 33. Now, a vessel coagulation takes place in the zones 34, 36. Due to the power concentration at the band edges 28, 31, a coagulation, desiccation and severing of the tissue occurs in the cutting zone 35 concentrated in a small region.

After performing the coagulation, it is possible—in order to support the cutting operation—to apply a higher voltage to the electrode surface 23a and the counter-electrode surface 25a, in that the switch device 38 is activated. At the same time, the electrode surface 22a and the counter-electrode surface 26a can be deactivated or (also be further) operated. Due to the higher voltage in the cutting region 35, already coagulated tissue in this region can be severed, in which case the cut that forms is bordered by the coagulation seams that have formed in the coagulation zones 34 and 36.

In this manner, a fusion instrument is provided that does not comprise a cutting electrode or knife, that is self-centering and configured extremely delicately FIG. 10 illustrates another modification of a fusion instrument having two jaws 22, 23 having, for example, a circular cross-section and two counter-jaws 25, 26 having, for example, also a circular cross-section. The jaws 22, 23 are arranged on a line 40 that is oriented at an acute angle relative to the direction of movement B. In a like manner, the counter-jaws 25, 26 are arranged on a line 41 that is also arranged obliquely relative to the direction of movement B and is preferably parallel to the line 40. Considering this configuration, the cutting gap is narrower than the coagulation gap 34, 36. As a result of this and as a result of the effect of the insulators 27, 30, the current density in the middle cutting gap 35 may be greater than in the lateral coagulation gaps 34, 36, so that a fast and secure severing of the tissue can be provoked in the cutting gap 35.

Figure 11:
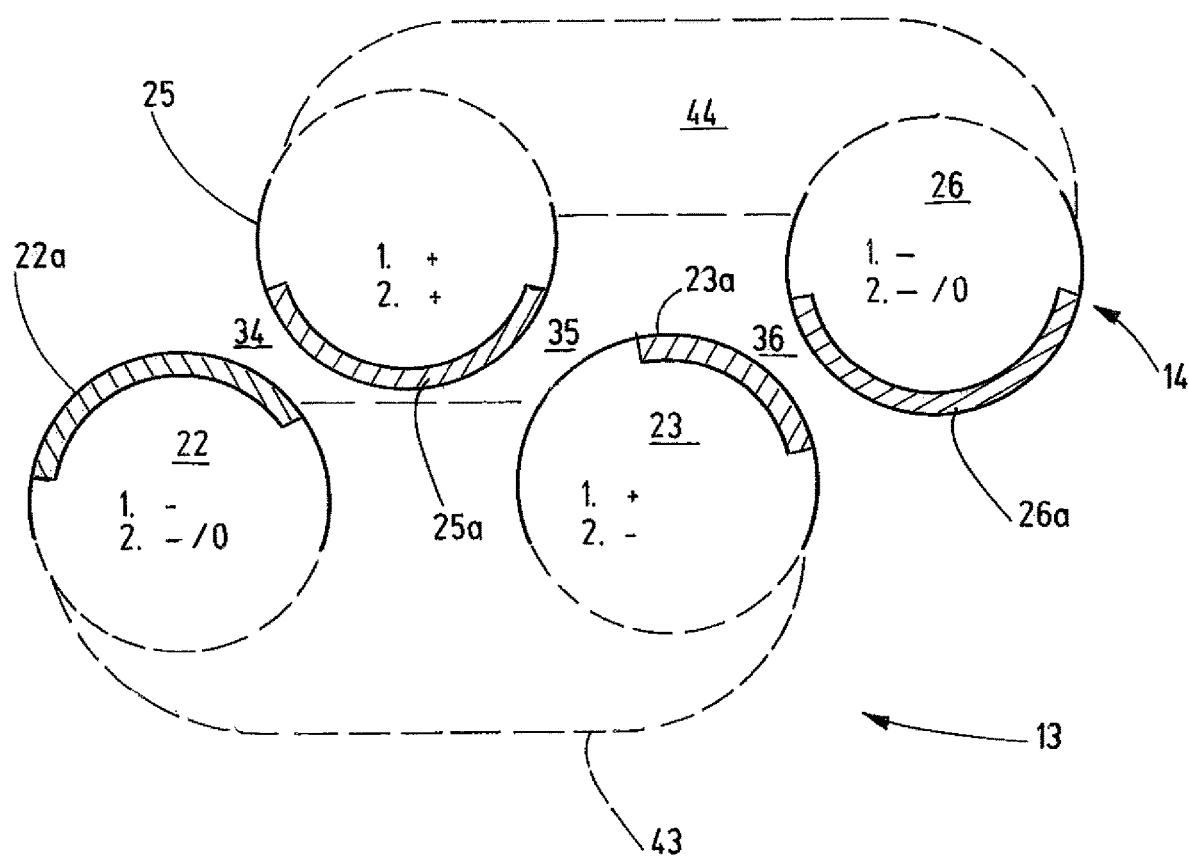
FIG. 11 schematized cross-sectional representations of a jaw and counter-jaw arrangement with an illustration of the energization in different phases of operation.

FIG. 11 illustrates a design modification that can be applied to all the instruments described hereinabove. It is indeed possible to structurally combine the jaws 22, 23, in that a bridge 43 is provided between the two. For example, the jaws 22, 23 and the bridge 43 are formed by a formed plastic component that is provided with sheet metal or electrically conductive formed parts that form the electrode surfaces 22a, 23a. Additionally or alternatively, the counter-jaws 25, 26 may be connected by a bridge 44 that—together with the counter-jaws 25, 26—forms a formed component, e.g., of plastic material, provided with the electrodes 25a, 26a. The electrodes 25a, 26a, in turn, may be sheet metal or electrically conductive formed parts. In the jaw arrangement 13, the jaws 22, 23 are represented by regions or slightly elevated rib-like sections of the formed part. In the counter-jaw arrangement 14, the jaws 25, 26 are also formed by regions or slightly elevated rib-like sections of the formed part.

Furthermore, advantageous processes of a coagulation and cutting operation can be inferred from FIG. 11, which process can also be employed with the instruments according to FIGS. 7 and 10:

First, a coagulation using RF power on the instrument is performed consistent with the polarity stated at 1. In doing so, the coagulation gaps 34 and 36 are electrically perfused, while the cutting gap 35 remains currentless. A first terminal of the source is in contact with the electrode 23a and the electrode 25a of the counter-jaw 25, whereas the other terminal of the source is in contact with the electrode 22a and the counter-electrode 26a of the counter-jaw 26. While the biological tissue in the coagulation gaps 34, 36 is coagulated and fused, said tissue remains initially fresh in the cutting gap 35.

Cutting occurs with one terminal on 25a and other terminal on 23a. During the cutting operation, the electrodes 22a and 26a are floating, in which case said cutting operation may occur subsequently.

The difference may not appear important, however, the fact is that previously coagulated tissue now is harder to cut by electrical means. Therefore, it is also of decisive importance for the tissue in the region 35 to desiccate as little as possible prior to cutting.

The instrument 10 according to the invention comprises a jaw arrangement 13 with two jaws 22, 23 that have, on their side facing the counter-electrode arrangement 14, rounded and/or also flat electrode surfaces 22a, 23a. The counter-electrode arrangement 14 comprises at least one counter-electrode surface 25a that is also configured so as to be rounded and/or flat. One of the electrode surfaces 22a, 23a has a band edge 28 that is preferably bordered by an insulator 27, on one side, said band edge being adjacent to the adjacent electrode surface 22a of the jaw arrangement 13. The counter-electrode surface 25a, likewise, has a band edge 31 adjacent to the insulator 30, said band edge facing the band edge 28. The band edges 28, 31 of the electrode surfaces 23a, 25a acting as the coagulation surfaces are close enough to each other (0.1 mm to 0.75 mm) that they form cutting edges that, in the ideal case, develop a cutting effect with low voltages that are otherwise suitable only for coagulation. Considering this concept, it is possible to provide fusion instruments that are curved in longitudinal direction, are extremely delicate, display lower thermal inertia and provide an excellent fusion and cutting effect.

LIST OF REFERENCE SIGNS

| | |
|---|---|
| 10 | Instrument |
| 11 | Shaft |
| 12, 12` | Tool |
| 14 | Counter-jaw arrangement |
| 13 | Jaw arrangement |
| 15 | Axis |
| 16 | Handle |
| 17 | Actuating lever |
| 18 | Actuating lever |
| 19 | Cable |
| 20 | Apparatus |
| 22, 22` | First jaw |
| 22a | Electrode surface of the first jaw 22 |
| 23, 23` | Second jaw |
| 23a | Electrode surface of the second jaw 23 |
| 25, 25`, 25`` | First counter-jaw |
| 25a, 25a` | Counter-electrode surface of the counter-jaw 25, 25` |
| 26 | Second counter-jaw |
| D1 | Diameter of the cross-section of the first jaw 22 |
| D2 | Diameter of the cross-section of the second jaw 23 |
| A | Distance of the jaws 22, 23 from each other |
| A1 | Distance of the band edges 28, 30 from each other |
| A2 | Distance of the counter-jaws 25, 26 from each other |
| R | Direction of movement |
| E, E1 | Center line |
| D3 | Diameter of the cross-section of the counter-jaw 25 |
| 27 | Insulator |
| 28 | Band edge |
| 30 | Insulator |
| 31 | Band edge |
| 32 | Tissue, vessel |
| 33 | Source |
| M | Center distance |
| 34 | Left coagulation region |
| 35 | Cutting region |
| 36 | Right coagulation region |
| 26a | Counter-electrode surface of the counter-jaw 26 |
| 38 | Switch device |
| 39 | Transformer |
| 40, 41 | Line |
| 42 | Connection and corner, respectively, on the polygonal counter-jaw 25`` |
| $A_m$ | Center distance in FIG. 6 |

The invention claimed is:

1. An instrument for the sealing and cutting of vessels, comprising:
a jaw arrangement including a first jaw having a first electrode surface and a second jaw having a second electrode surface, said first and second jaws being held at a distance from each other;
a counter-jaw arrangement including at least one counter-jaw;
wherein the first electrode surface of the first jaw and the second electrode surface of the second jaw are arranged in an asymmetric manner with respect to a longitudinally extending central plane that is parallel to a direction of movement of the respective first or second jaw or the counter-jaw and which extends through a cross-sectional center of the jaw and counter-jaw arrangements, and/or an electrode surface of the counter-jaw is arranged in an asymmetric manner with respect to the longitudinally extending central plane;
wherein the electrode surfaces of the second jaw and the at least one counter-jaw are configured to form a cutting gap therebetween for electrically cutting tissue disposed therein;
wherein the electrode surfaces of the first jaw and the at least one counter jaw are configured to form a coagulation gap therebetween for electrically sealing or coagulating tissue disposed therein;
wherein the second electrode surface of the second jaw of the jaw arrangement is electrically conductive and the second jaw includes an insulated section disposed on a side of the second jaw facing the first jaw;
wherein the electrically conductive electrode surface of the second jaw of the jaw arrangement has a current-concentrated edge adjacent the insulated section configured for cutting tissue disposed in the cutting gap between the current-concentrated edge and the electrode surface of the at least one counter-jaw;
wherein the first electrode surface of the first jaw is electrically conductive and is configured for sealing or coagulating tissue disposed in the coagulation gap between the first electrode surface and the electrode surface of the at least one-counter jaw.

2. The instrument according to claim 1, wherein the electrode surface of the counter-jaw is electrically conductive and the counter-jaw includes an electrically insulated counter section disposed on a side facing away from the first jaw.

3. The instrument according to claim 1, wherein the counter-jaw has a convexly curved surface facing the first and second jaws, and each of the first and second jaws has a convexly curved surface facing the counter-jaw, and wherein a distance between the first jaw and the second jaw is smaller than a diameter of the counter-jaw.

4. The instrument according to claim 1, wherein the counter-jaw has a center located on the central plane and the first and second jaws of the jaw arrangement are arranged on different sides of the central plane at equal distances therefrom.

5. The instrument according to claim 1, wherein the counter-jaw and the first and second jaws each have a cross-sectional surface area, and the cross-sectional surface area of the counter-jaw is at most as large as the sum of the cross-sectional surface areas of the first and second jaws.

6. The instrument according to claim 2, wherein the electrically conductive electrode surface of the counter-jaw of the counter-jaw arrangement has a current-concentrating edge adjacent the insulated counter section.

7. The instrument according to claim 1, wherein the first electrode surface and the second electrode surface are electrically connected to each other.

8. The instrument according to claim 1, wherein the counter-jaw arrangement includes two counter-jaws that are held at a distance from each other.

9. The instrument according to claim 1, wherein the first and second jaws of the jaw arrangement and the at least one counter-jaw of the counter-jaw arrangement are arranged so as to be laterally offset relative to each other.

10. The instrument according to claim 8, wherein the counter-jaws have counter-electrode surfaces that are connected to each other.

11. The instrument according to claim 1, wherein the electrode surfaces of the jaw arrangement are configured to be energized with different voltages with respect to one another.

12. The instrument according to claim 1, wherein the counter-jaw arrangement comprises two counter-electrodes including the electrode surface of the counter-jaw that are configured to be energized with different voltages with respect to one another.

13. The instrument according to claim 1, wherein the counter-jaw arrangement comprises two counter-electrode surfaces including the electrode surface of the counter-jaw that define, with the electrode surfaces of the first and second jaws, two coagulation gaps and one cutting gap.

14. The instrument according to claim 1, wherein the first electrode surface extends along a side of the first jaw facing the second jaw and the first jaw lacks an insulated section disposed on the side of the first jaw facing the second jaw.

* * * * *